United States Patent [19]
Fink et al.

[11] Patent Number: 5,217,982
[45] Date of Patent: Jun. 8, 1993

[54] COMPOUNDS HAVING ANTIHYPERTENSIVE PROPERTIES

[75] Inventors: Cynthia A. Fink, Doylestown; Alfred P. Spada, Lansdale, both of Pa.

[73] Assignee: Rhone-Poulenc Rorer Pharmaceuticals Inc., Collegeville, Pa.

[21] Appl. No.: 614,323

[22] Filed: Nov. 15, 1990

Related U.S. Application Data

[63] Continuation-in-part of Ser. No. 587,884, Sep. 25, 1990.

[51] Int. Cl.$^5$ .................. A61K 31/44; C07D 213/02
[52] U.S. Cl. .................. 514/352; 514/187; 514/255; 514/269; 514/353; 514/369; 514/372; 514/427; 514/445; 546/308; 546/309; 546/153; 546/155; 546/156; 544/298; 544/299; 544/301; 544/303; 544/408; 548/541; 548/542; 548/544; 548/545; 548/546; 564/167
[58] Field of Search ............. 546/308, 309; 514/353, 514/352

[56] References Cited

U.S. PATENT DOCUMENTS

| | | | |
|---|---|---|---|
| Re. 31,244 | 5/1983 | Petersen | 514/313 |
| 4,098,903 | 7/1978 | Fountain et al. | 546/308 |
| 4,148,913 | 4/1979 | Szmuszkovicz | 514/489 |
| 4,156,015 | 5/1979 | Szmuszkovicz | 514/613 |
| 4,159,340 | 6/1979 | Szmuszkovicz | 514/485 |
| 4,204,003 | 5/1980 | Szmuszkovicz | 424/324 |

FOREIGN PATENT DOCUMENTS 0268878A 5/1988 European Pat. Off. .

OTHER PUBLICATIONS

Houston et al, J. Med. Chem., 1985, vol. 28, No. 4, 467–477.
Bowman, et al., Synthesis of Flufenamic Acid Metabolites I and II and Other N-Arylanthranilic Acids; J. Chem. Soc. Perkin Trans. 1, (1), 1–4 (1973).
Synthesis of 3-Deazaclitocine [2-amino-3-nitro-4-(-β-D-ribofuranosylamino)pyridine] as Cytotoxic Agent; Nucleosides & Nucleotides, 10 (1–3), 543–545 (1991).
Baxter, et al., Synthesis and Biological Activity of Carbocyclic clitocine; Nucleosides & Nucleotides, 10 (1–3), 393–396 (1991).

*Primary Examiner*—Glennon H. Hollrah
*Assistant Examiner*—Shailendra Kumar
*Attorney, Agent, or Firm*—Paul R. Darkes; Martin F. Savitzky

[57] ABSTRACT

This invention relates to compounds which are derivatives of cyclopentane which are useful as antihypertensive agents, to pharmaceutical compositions including such compounds, and to their use in treating hypertension.

12 Claims, No Drawings

COMPOUNDS HAVING ANTIHYPERTENSIVE PROPERTIES

This application is a continuation-in-part application of U.S. patent application Ser. No. 7/587,884, filed Sep. 25, 1990.

BACKGROUND OF THE INVENTION

1. Field of the Invention

This invention relates to compounds which are derivatives of cyclopentane, to pharmaceutical compositions containing such compounds and to their use in treating hypertension.

Hypertension

Hypertension, a condition of elevated blood pressure, affects a substantial number of the human population. Consequences of persistent hypertension include vascular damage to the ocular, renal, cardiac and cerebral systems, and the risk of these complications increases as blood pressure increases. Basic factors controlling blood pressure are cardiac output and peripheral vascular resistance, with the latter being the predominant common mechanism which is controlled by various influences. The sympathetic nervous system regulates peripheral vascular resistance through direct effects on alpha- and beta-adrenergic receptors as well as through indirect effects on renin release. Drug therapy is aimed at specific components of these blood pressure regulatory systems, with different mechanisms of action defining the several drug classes including diuretics, beta-adrenergic receptor antagonists (beta-blockers), angiotensin-converting enzyme (ACE) inhibitors, and calcium channel antagonists.

Thiazide-type diuretics are used in hypertension to reduce peripheral vascular resistance through their effects on sodium and water excretion. This class of drugs includes hydrochlorothiazide, chlorothiazide, methyclothiazide, and cyclothiazide, as well as related agents indapamide, metolazone, and chlorthalidone. Although the beta-blocker mechanism of action was once believed to be blockade of the $beta_1$-adrenergic receptor subtype in the heart to reduce heart rate and cardiac output, more recent beta-blockers with intrinsic sympathomimetic activity (ISA), including pindolol, acebutolol, penbutolol, and carteolol, are as effective as non-ISA beta-blockers, causing less reduction in heart rate and cardiac output. Other postulated mechanisms for these drugs include inhibition of renin release, a central effect, and an effect at pre-synaptic beta-adrenergic receptors resulting in inhibition of norepinephrine release. Cardioselective beta-blockers metoprolol (Lopressor-Geigy), acebutolol (Sectral-Wyeth), and atenolol (Tenormin-ICI), at low doses, have a greater effect on $beta_1$-adrenergic receptors than on $beta_2$-adrenergic receptor subtypes located in the bronchi and blood vessels. Nonselective beta-blockers act on both beta-adrenergic receptor subtypes and include propranolol (Inderal-Ayerst), timolol (Blocadren-Merck), nadolol (Corgard-Squibb), pindolol (Visken-Sandoz), penbutolol (Levatol-Hoechst-Roussel), and carteolol (Cartrol-Abbott). Adverse effects of beta-blockers include asymptomatic bradycardia, exacerbation of congestive heart failure, gastrointestinal disturbances, increased airway resistance, masked symptoms of hypoglycemia, and depression. They may cause elevation of serum triglycerides and may lower high-density lipoprotein cholesterol.

ACE inhibitors prevent the formation of angiotensin II and inhibit breakdown of bradykinin. Angiotensin II is a potent vasoconstrictor and also stimulates the secretion of aldosterone. By producing blockade of the renin-angiotensin-aldosterone system, these agents decrease peripheral vascular resistance, as well as sodium and water retention. In addition, ACE inhibitors increase levels of bradykinin and prostaglandins, endogenous vasodilators. Captopril (Capoten-Squibb) and Enalapril (Vasotec-Merck) are the leading ACE inhibitors. Adverse effects of the ACE inhibitors include rash, taste disturbance, proteinuria, and neutropenia.

The calcium channel antagonists reduce the influx of calcium into vascular smooth muscle cells and produce systemic vasodilation, resulting in their antihypertensive effect. Other effects of calcium channel antagonists include interference with action of angiotensin II and $alpha_2$-adrenergic receptor blockade, which may add to their antihypertensive effects. Calcium channel antagonists do not have the adverse metabolic and pharmacologic effects of thiazides or beta-blockers and may therefore be useful in patients with diabetes, peripheral vascular disease, or chronic obstructive pulmonary disease. Two calcium channel antagonists, Verapamil and diltiazem, have serious adverse cardiovascular effects on atrioventricular cardiac conduction in patients with preexisting conduction abnormalities, and they may worsen bradycardia, heart block, and congestive heart failure. Other minor adverse effects of calcium channel antagonists include peripheral edema, dizziness, light-headedness, headache, nausea, and flushing, especially with nifedipine and nicardipine.

Many other agents are available to treat essential hypertension. These agents include prazosin and terazocin, $alpha_1$-adrenergic receptor antagonists whose antihypertensive effects are due to resultant arterial vasodilation; clonidine, an $alpha_2$-adrenergic agonist which acts centrally as well as peripherally at inhibitory $alpha_2$-adrenergic receptors, decreasing sympathetic response. Other centrally acting agents include methyldopa, guanabenz, and guanfacine; reserpine, which acts by depleting stores of catecholamines; guanadrel, a peripheral adrenergic antagonist similar to guanethidine with a shorter duration of action; and direct-acting vasodilators such as hydralazine and minoxidil. These agents, although effective, produce noticeable symptomatic side effects, including reflex sympathetic stimulation and fluid retention, orthostatic hypotension, and impotence.

Many antihypertensive agents activate compensatory pressor mechanisms, such as increased renin release, elevated aldosterone secretion and increased sympathetic vasoconstrictor tone, which are designed to return arterial pressure to pretreatment levels, and which can lead to salt and water retention, edema and ultimately to tolerance to the antihypertensive actions of the agent. Furthermore, due to the wide variety of side effects experienced with the present complement of antihypertensive drugs and the problems experienced therewith by special populations of hypertensive patients, including the elderly, blacks, and patients with chronic obstructive pulmonary disease, diabetes, or peripheral vascular diseases, there is a need for additional classes of drugs to treat hypertension.

The present invention relates to a class of novel cyclopentane derivatives and their utility in the treatment of hypertension.

2. Reported Developments

Cyclopentane compounds are reported in the literature.

A series of N-[2-(dialkylamino)cyclopentyl]anilines, limited to 1,2-disubstitution on the cyclopentane ring, are reported as intermediates to N-(2-aminocyclopentyl)-N-alkanoylanilides which are described as CNS antidepressants, U.S. Pat. Nos. 4,204,003; 4,148,913; 4,156,015; and 4,159,340.

N-arylaminocycloalkanols, including 1- and 2-methyl-2-(arylamino)cyclopentanol where aryl is phenyl, o-, m-, and p-tolyl, is reported by Kuliev, et al., *Azerb. Khim. Zh.* 1977, (3), 66–70; *Azerb. Khim. Zh.* 1978, (1), 56–60.

2-nitro-N-cyclopentylaniline is disclosed in Gladys, et al., *Chem. Bar.*, 107(11), 3658-73, and 2-(cyclopentylamino) benzoic acid is disclosed in Bowman, et al., *J. Chem. Soc.* Perkin Trans. 1, (1), 1–4 (1973).

$4\beta$-(3-nitro-4-pyridyl)amino-$2\alpha,3\alpha$-dihydroxy-$1\beta$-cyclopentanemethanol and $4\beta$-(2-chloro-3-amino-4-pyridyl)amino-$2\beta,3\beta$-dihydroxy-$1\beta$-cyclopentanemethanol are disclosed in D. M. Houston, et al., *J. Med. Chem.* 1985, 28 (4), 471 (1985), as intermediates in the synthesis of a series of inhibitors of S-adenosylhomocysteine hydrolase, although there is no disclosure that these intermediates exhibit any biological activity.

Cyclopentane analogs of adenosine, containing a modified purine moiety, have been reported to exhibit antihypertensive activity which is attributed to the cyclopentane analog's binding affinity for one or more of the known adenosine receptors, EP Published Application No. 0267878. Cyclopentane adenosine analogs exhibiting antihypertensive activity and $A_1/A_2$ adenosine receptor binding affinities are reported in co-pending U.S. application Ser. No. 7/587,884, filed Sep. 25, 1990, assigned to the same assignee as the present application, in which certain compounds of the present invention are disclosed as starting materials for the preparation of adenosine analogs.

Compounds of the present invention exhibit antihypertensive activity but, in contrast to the aforementioned adenosine analogs, do not possess significant affinity for either the $A_1$ or $A_2$ adenosine receptors.

SUMMARY OF THE INVENTION

The compounds of the present invention are described by Formula I

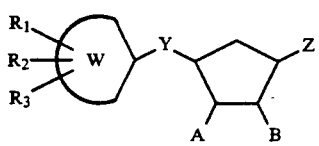

Formula I wherein:

is a carbocyclic or heterocyclic ring containing about four to about ten carbon atoms and 0 to about two heteroatoms such as N, O, or S;

$R_1$, $R_2$, and $R_3$ are independently nitro, cyano, carboxy, carboalkoxy, carboaryloxy, carboaralkoxy, carbamoyl, alkylcarbamoyl, dialkylcarbamoyl, thiocarbamoyl, alkylthiocarbamoyl, dialkylthiocarbamoyl, halo, alkoxy, alkylthio, acyl, aryl, alkyl, amino, alkylamino, dialkylamino or hydrogen;

Y is oxygen, sulfur, or —$NR_y$— where $R_y$ is hydrogen or alkyl;

A and B are independently hydrogen, hydroxy, alkoxy, aralkoxy, aryloxy, mercapto, alkylthio, arylthio, aralkylthio, amino, alkylamino, dialkylamino or halo, provided that A and B are not both hydrogen; and Z is carbamoyl, alkylcarbamoyl, dialkylcarbamoyl, thiocarbamoyl, alkylthiocarbamoyl, dialkylthiocarbamoyl, mercaptomethyl, alkylthiomethyl, alkoxymethyl, aryloxymethyl, arylthiomethyl, alkoxy, aryloxy, aralkoxy, amino, alkylamino, dialkylamino, mercapto, alkylthio, cyano, carboxy, carboalkoxy, carboaralkoxy, carboaryloxy, alkyl, aryl, aminomethyl, alkylaminomethyl or dialkylaminomethyl;

This invention relates also to methods for treating cardiovascular disease marked by hypertension using pharmaceutical compositions including an antihypertensive effective amount of a compound of the above formula.

DETAILED DESCRIPTION

As used above and throughout the description of this invention, the following terms, unless otherwise indicated, shall be understood to have the following meanings:

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred alkyl groups are the "lower alkyl" groups which are those alkyl groups having from 1 to about 6 carbons.

"Acyl" means an

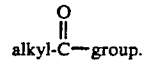

group.

Preferred acyl groups are those in which the alkyl group is lower alkyl.

"Alkylamino" means an alkyl-NH- group. Preferred groups are lower alkylamino groups.

"Alkylcarbamoyl" means an

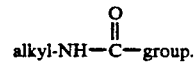

group.

Preferred groups are lower alkylcarbamoyl.

"Alkylthio" means an alkyl-S- group. Preferred groups are lower alkylthio.

"Alkylthiocarbamoyl" means an

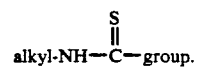

group.

Preferred groups are lower alkylthiocarbamoyl.

"Alkoxy" means an alkyl-O- group. Lower alkoxy groups are preferred. Exemplary groups include methoxy, ethoxy, n-propoxy, i-propoxy and n-butoxy.

"Aralkyl" means an alkyl group substituted by an aryl radical, wherein "aryl" means a phenyl or phenyl substituted with one or more substituents which may be alkyl, alkoxy, amino, nitro, carboxy, carboalkoxy, cyano, alkylamino, halo, hydroxy, hydroxyalkyl, mercapto, alkylthio, acyl, or carbamoyl. Exemplary groups include benzyl and phenethyl.

"Aralkoxy" means an aralkyl-O- group. Exemplary groups include benzyloxy and phenethyloxy.

"Aryloxy" means an aryl-O- group. Exemplary groups include phenoxy and 2-naphthyloxy.

"Carboalkoxy" means an

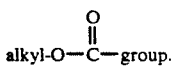

Preferred carboalkoxy groups are those in which the alkyl group is lower alkyl.

"Carboaralkoxy" means an

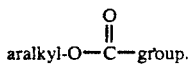

Preferred groups include carbobenzyloxy and carbophenethyloxy.

"Carboaryloxy" means an

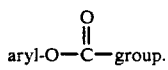

Preferred groups include carbophenoxy and carbo-2-naphthyloxy.

"Dialkylamino" is an

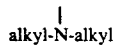

group where the alkyl groups may be the same or different. Preferred dialkylamino groups are those in which the alkyl groups are lower alkyl.

"Dialkylcarbamoyl" is an

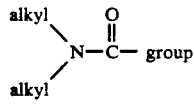

where the alkyl groups may be the same or different. Preferred dialkylcarbamoyl groups are those in which the alkyl groups are lower alkyl.

"Dialkylthiocarbamoyl" is an

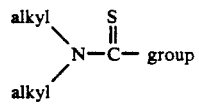

where the alkyl groups may be the same or different. Preferred dialkylthiocarbamoyl groups are those in which the alkyl groups are lower alkyl.

"Halogen" (or "halo") means chlorine (chloro), fluorine (fluoro), bromine (bromo) or iodine (iodo).

It should be understood that Formula 1 covers compounds wherein the

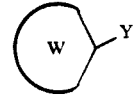

moiety is formed by stable carbon-hetero atom bonds wherein the Y group is bonded to carbon atoms only. Accordingly, the Y group does not form an O—O, O—S, N—O, N—S, N—N, or S—S bond with the

group.

The compounds of Formula I contain asymmetric centers on the cyclopentane ring at the carbon atoms where Y and Z are attached, and where A and B are attached when A or B are not hydrogen. These asymmetric centers may independently be in either the R or S configuration. The present invention includes the individual stereoisomers and mixtures thereof.

The compounds of the present invention may be used in the form of the free base, in the form of acid addition salts or as hydrates. All such forms are within the scope of this invention. Acid addition salts are simply a more convenient form for use. In practice, use of the salt form inherently amounts to use of the base form. The acids which may be used to prepare the acid addition salts include preferably those which produce, when combined with the free base, pharmaceutically acceptable salts, that is, salts whose anions are non-toxic to the recipient in pharmaceutical doses of the salts, so that the beneficial anti-hypertensive effect produced by the free base is not vitiated by side effects ascribable to the anions. Although pharmaceutically acceptable salts of the compounds of this invention are preferred, all acid addition salts are useful as sources of the free base form, even if the particular salt, per se, is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of this invention are those derived from the following acids: mineral acids such as hydrochloric acid, hydrobromic acid, sulfuric acid, phosphoric acid, and sulfamic acid; and organic acids such as acetic acid, citric acid, lactic acid, tartaric acid, malonic acid, methanesulfonic acid, fumaric acid, ethanesulfonic acid, benzenesulfonic acid, p-toluenesulfonic acid, cyclohexysulfamic acid, salicyclic acid, quinic acid and the like. The corresponding acid addition salts comprise the following: hydrochloride, hydrobromide, sulfate, phosphate, sulfamate, acetate, citrate, lactate, tartarate, malonate, methanesulfonate, fumarate, ethanesulfonate, benzenesulfonate, p-toluenesulfonate, cyclohexylsulfamate, salicylate, and quinate, respectively.

The acid addition salts of the compounds of the invention are conveniently prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Exemplary carbocyclic and heterocyclic groups include phenyl, naphthyl, pyridyl, quinolinyl, pyrimidyl, pyrrolyl, thiazolinyl, thienyl, or pyrazinyl, which groups are optionally substituted with $R_1$, $R_2$, and $R_3$ as hereinbefore defined.

A preferred class of compounds of this invention is described by Formula I wherein

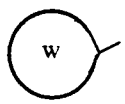

is an aromatic heterocyclic ring.

A more preferred class of compounds is described where the heterocyclic ring is pyridyl, quinolinyl, or pyrimidyl.

The most preferred class of compounds of this invention comprises compounds of Formula I wherein the heterocyclic ring is pyridyl, quinolinyl, or pyrimidyl; $R_1$, $R_2$, and $R_3$ are independently nitro, cyano, carboxy, carboalkoxy, carboaryloxy, carboaralkoxy, carbamoyl, alkylcarbamoyl, dialkylcarbamoyl, thiocarbamoyl, alkylthiocarbamoyl or dialkylthiocarbamoyl; Y is —$NR_y$— where $R_y$ is hydrogen or alkyl; A and B are independently hydrogen, hydroxy, mercapto, amino or fluoro provided that A and B are not both hydrogen; and Z is carbamoyl, alkylcarbamoyl, dialkylcarbamoyl, thiocarbamoyl, alkylthiocarbamoyl or dialkylthiocarbamoyl.

A special embodiment of this invention comprises compounds of the most preferred class where the heterocyclic group is substituted by at least one nitro or cyano substituent.

Representative compounds of the present invention include: 4$\beta$-(2-pyridyl)amino-2$\alpha$,3$\alpha$-dihydroxycyclopentane-1$\beta$-N-ethylcarboxamide; 4$\beta$-(3-nitro-2-pyridyl)amino-2$\alpha$,3$\alpha$-dihydroxycyclopentane-1$\beta$-N-ethylcarboxamide; (−)-4$\beta$-(3-nitro-2-pyridyl)amino-2$\alpha$,3$\alpha$-dihydroxycyclopentane-1$\beta$-N-ethylcarboxamide; (+)-4$\beta$-(3-nitro-2-pyridyl)amino-2$\alpha$,3$\alpha$-dihydroxycyclopentane-1$\beta$-N-ethylcarboxamide; 4$\beta$-(3-cyano-2-pyridyl)amino-2$\alpha$,3$\alpha$-dihydroxycyclopentane-1$\beta$-N-ethylcarboxamide; 4$\beta$-(4-amino-3-nitro-2-pyridyl)amino-2$\alpha$,3$\alpha$-dihydroxycyclopentane-1$\beta$-N-ethylcarboxamide; 4$\beta$-(2-nitrophenyl)amino-2$\alpha$,3$\alpha$-dihydroxycyclopentane-1$\beta$-N-ethylcarboxamide; 4$\beta$-(4-nitro-2-pyridyl)amino-2$\alpha$,3$\alpha$-dihydroxycyclopentane-1$\beta$-N-ethylcarboxamide; 4$\beta$-(3-Methyl-4-nitro-2-pyridyl)amino-2$\alpha$,3$\alpha$-dihydroxycyclopentane-1$\beta$-N-ethylcarboxamide; 4$\beta$-(3-nitro-2-thienyl)amino-2$\alpha$,3$\alpha$-dihydroxycyclopentane-1$\beta$-N-ethylcarboxamide; 4$\beta$-(5-nitro-2-thienyl)amino-2$\alpha$,3$\alpha$-dihydroxycyclopentane-1$\beta$-N-ethylcarboxamide; 4$\beta$-(3-nitro-2-quinolinyl)amino-2$\alpha$,3$\alpha$-dihydroxycyclopentane-1$\beta$-N-ethylcarboxamide; 4$\beta$-(2-pyrimidyl)amino-2$\alpha$,3$\alpha$-dihydroxycyclopentane-1$\beta$-N-ethylcarboxamide; and 4$\beta$-(2-pyrazinyl)amino-2$\alpha$,3$\alpha$-dihydroxycyclopentane-1$\beta$-N-ethylcarboxamide.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention, generally, are available by reaction of an appropriately substituted cyclopentyl amine, mercaptan, or alcohol with an appropriately substituted carbocyclic or heterocyclic halide in the presence of a base, either neat or in a solvent, as shown in Scheme I below.

Scheme I

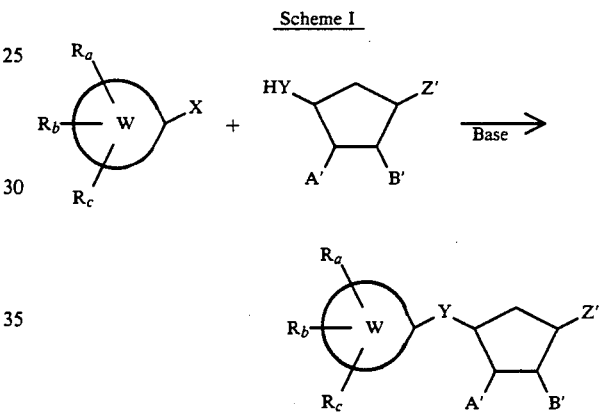

X is halo, preferably chloro, bromo, or fluoro; $R_a$, $R_b$, $R_c$, A′, B′, and Z′ are $R_1$, $R_2$, $R_3$, A, B, and Z, respectively, protected analogs thereof, or precursor substituents thereto.

As noted above, preferred compounds encompass aromatic

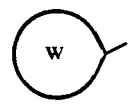

groups. Their preparation pursuant to Scheme I is facilitated by activation of the halide, X, towards displacement by having an electron withdrawing substituent group, $R_a$, $R_b$, $R_c$, such as nitro or cyano in a position on the aromatic ring ortho or para to the halogen. These activating groups may be retained in the final product, if desired, or may be subjected to further reaction, in order to convert the activating group to the desired substituent or to remove it, by known methods. An exemplary conversion of a cyano activating group to other desired derivatives is shown in Scheme II below.

Scheme II

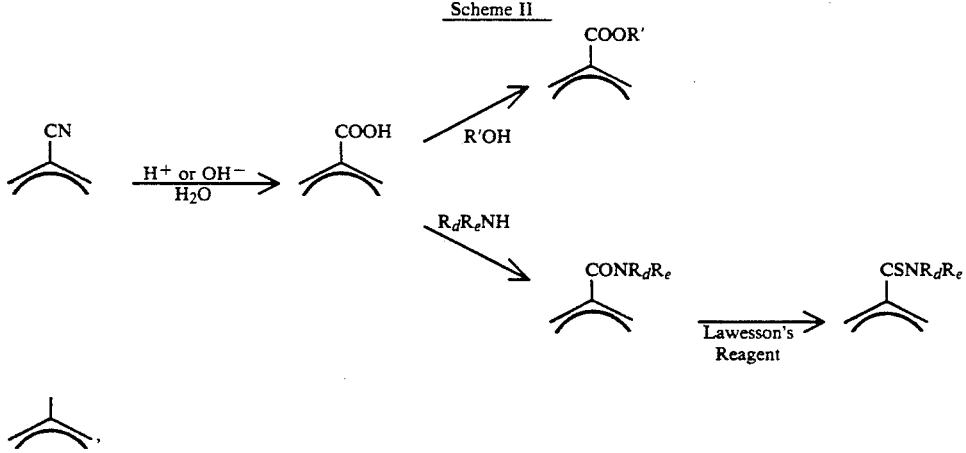

represents the desired aromatic group, R' is alkyl, aryl, or aralkyl and $R_d$ and $R_e$ are independently hydrogen or alkyl.

The aromatic nitrile may be hydrolyzed to the corresponding carboxylic acid which may, in turn, be esterified to the desired carboalkoxy, carboaryloxy, or carboaralkoxy groups. Alternately, the carboxylic acid may be converted to the desired carbamoyl, alkylcarbamoyl or dialkylcarbamoyl group by reaction with an appropriate amine which may be subsequently converted to the corresponding thiocarbamoyl function, for example, by use of Lawesson's Reagent (2,4-bis(4-methoxyphenyl)-1,3-dithia-2,4-disulfide).

The conversion of an activating nitro group is shown in Scheme III below.

chloro, or cyano by treatment with cuprous bromide and cuprous chloride and cuprous cyanide, respectively; iodo by treatment with iodide ion; and fluoro by treatment with tetrafluoroborate ion. The phenol and thiophenol may subsequently be alkylated to the alkoxide or alkylthio groups, respectively, by treatment with alkyl halides.

The amino group may be formylated with formic acid or acylated by treatment with the appropriate acyl anhydride or acyl chloride and subsequently reduced, for example with sodium borohydride, to the alkylamino derivative. This procedure may be repeated, if desired, to give the dialkylamino derivative. These conversions are shown in Scheme IV, below.

Scheme III

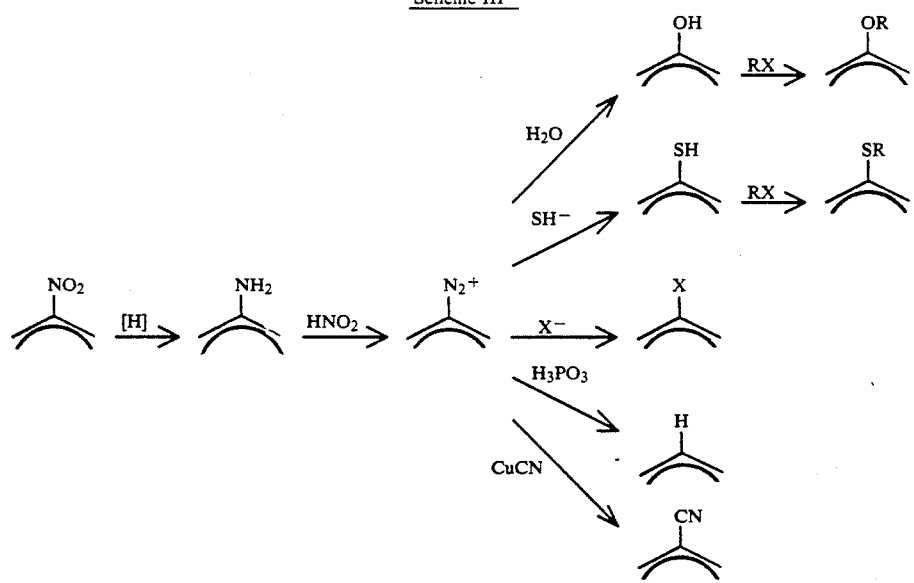

R is alkyl and X is halo.

The nitro group may be reduced to the amino group which can be converted to the diazonium salt by treatment with nitrous acid. The diazo group may be removed, for example, by treatment with hypophosphorous acid to give the unsubstituted derivative; or may be converted to the phenol by treatment with water; the thiophenol by treatment with sulfhydryl ion; bromo,

Scheme IV

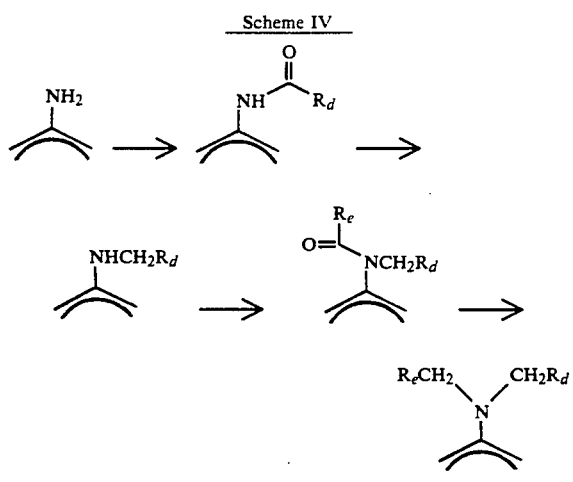

$R_d$ and $R_e$ are independently hydrogen or alkyl.

All of the above functional group conversions are well known in the art.

When the cylcopentane derivative starting material in the reaction in Scheme I is a cyclopentyl amine or mercaptan, the base to effectuate the coupling reaction is preferably an organic base such as triethylamine. The reaction may be neat, i.e., without a solvent, or in an organic solvent, preferably a polar solvent, for example methanol, ethanol, nitromethane, dimethylformamide, or n-butanol. When the aryl halide to be coupled is an aryl fluoride, the reaction is facilitated by the addition of potassium fluoride to the reaction mixture.

When the desired cyclopentane derivative starting material is a cyclopentyl alcohol, a base of sufficient strength to generate the anion of the alcohol must be employed. Exemplary bases include alkali metal t-butoxides, or sodium or potassium hydride, in an appropriate polar organic aprotic solvent such as tetrahydrofuran or dimethylformamide.

Other substituents desired on the aromatic ring or cyclopentane ring may be present at the time of coupling or may be introduced subsequently by standard procedures.

If it is necessary or desirable to prevent cross-reaction between chemically active substituents either on the aromatic ring or cyclopentyl ring, the substituents may be protected by standard blocking groups which may subsequently be removed by known methods to afford the desired product (see, for example, Greene, "Protective Groups in Organic Synthesis," Wiley, New York, 1991), as shown for the acetonide-protected α,α-dihydroxy cyclopentane starting material in Scheme V below.

Scheme V

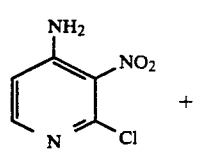
+
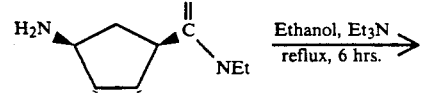

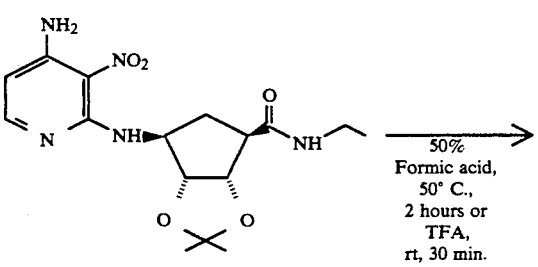

-continued
Scheme V

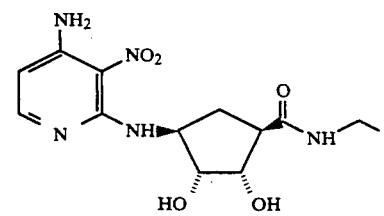

Following the coupling reaction, the protecting group is removed by treatment with formic acid or trifluoroacetic acid to give the final product.

Exemplary preparations of hydroxy and mercapto cyclopentyl starting materials for the preparations in Scheme I, above, are shown in Scheme VI below.

Scheme VI

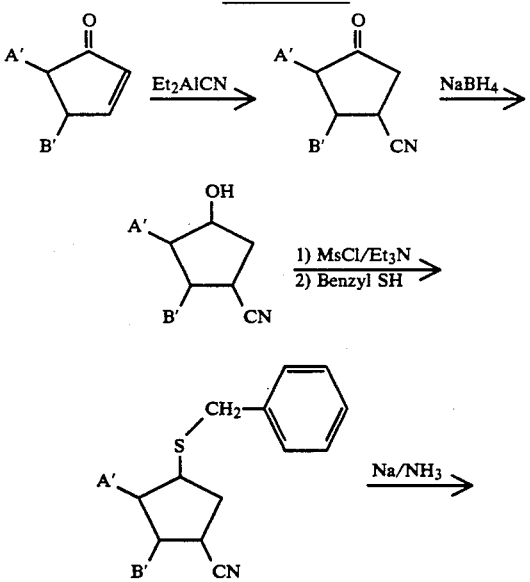

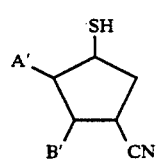

An appropriate cyclopentenone derivative is treated with diethylaluminum cyanide to give the β-cyanocyclopentanone which is reduced by treatment with sodium borohydride to the corresponding cyclopentyl alcohol. If the mercaptan is desired the alcohol may be converted to the mesylate by treatment with methanesulfonyl chloride, followed by treatment with benzyl mercaptan to give the benzylthio derivative. The benzyl group is then removed by treatment with sodium and liquid ammonia to afford the cyclopentyl mercaptan. If desired, the cyano group may be elaborated as discussed above to other functional groups at any appropriate point in the above scheme.

Exemplary preparations of cyclopentenone starting materials for the preparations in Scheme VI, above, are shown in Scheme VII below.

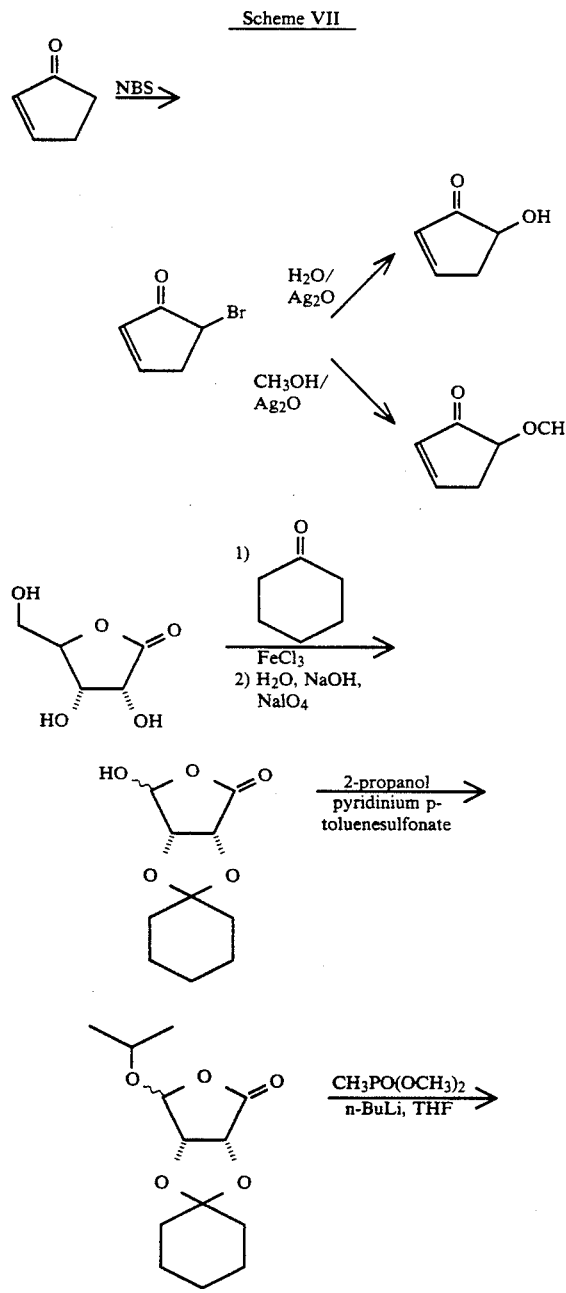

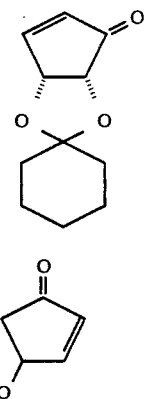

$R_g$ and $R_h$ are alkyl, aryl, aralkyl, hydrogen, or together form a cyclic alkylidene (e.g. isopropylidene), and $R_i$ is hydrogen, alkyl, aryl, or aralkyl.

Cyclopentenone is brominated in the alpha position by treatment with N-bromosuccinimide. The bromoketone is then treated with water or methanol in the presence of silver oxide to give 5-hydroxy or 5-methoxy cyclopenten-2-one, respectively, Wilson, et al., *Bioorganic Chemistry* 9, 212 (1980).

(−)-2,3-(cyclohexylidenedioxy)-4-cyclopentenone, a protected derivative of 4,5 dihydroxycyclopenten-2-one, is prepared in four steps from D-ribonolactone, Borcherding, et al., *J. Org. Chem.* 1987, 52, 5457. Treatment of the ribonolactone with cyclohexanone and ferric chloride, followed by treatment with water, sodium hydroxide, and sodium periodate gives the erythruronolactone which is treated with 2-propanol in the presence of pyridinium p-toluenesulfonate to give 2,3-(cyclohexylidenedioxy)-4-hydroxy-4-(2-propyloxy)-butanoic acid lactone. The lactone is treated with dimethyl methylphosphonate and n-butyllithium in tetrahydrofuran to give the desired cyclopentenone.

4-hydroxy, alkoxy, aralkoxy, and aryloxy cyclopenten-2-ones are prepared as described in Japan. Kokai 76 95042 (CA 86: 29430b) by acid hydrolysis of the corresponding cyclopentanone mercaptal S-oxides by treatment with sulfuric acid and water in diethyl ether.

Exemplary preparations of the amino cyclopentane starting materials for the preparations of Scheme I, above, are shown in Scheme VIII below.

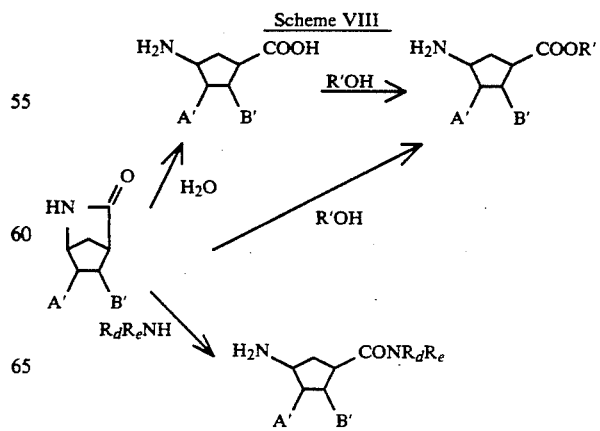

The lactam is opened by acid or base catalyzed hydrolysis to give the corresponding amino acid which may be subsequently treated with the appropriate alcohol or phenol to give the ester. Alternatively, the lactam may be treated with the alcohol or phenol to yield the amino ester directly.

The lactam may be opened with ammonia, an alkyl amine or dialkyl amine to give the corresponding amide derivative.

Exemplary preparations of lactam starting materials for Scheme VIII, above, are shown in Scheme IX below.

epoxide with hydrogen sulfide, alkyl, aryl or aralkyl mercaptans respectively.

Treatment of the azabicycloheptenone with hydrogen sulfide or an alkyl, aryl or aralkyl mercaptan in the presence of a free radical initiator such as peroxide, azo compounds or ultraviolet light prepares the corresponding mercaptan, alkylthio, arylthio, or aralkylthio compound, respectively, Griesbaum, *Angew Chem. Int. Ed. Engl.* 9, 273 (1970).

Free amino, mercapto, or hydroxy groups present on the cyclopentane ring after the preparations of Scheme VII or Scheme IX may be protected as discussed above

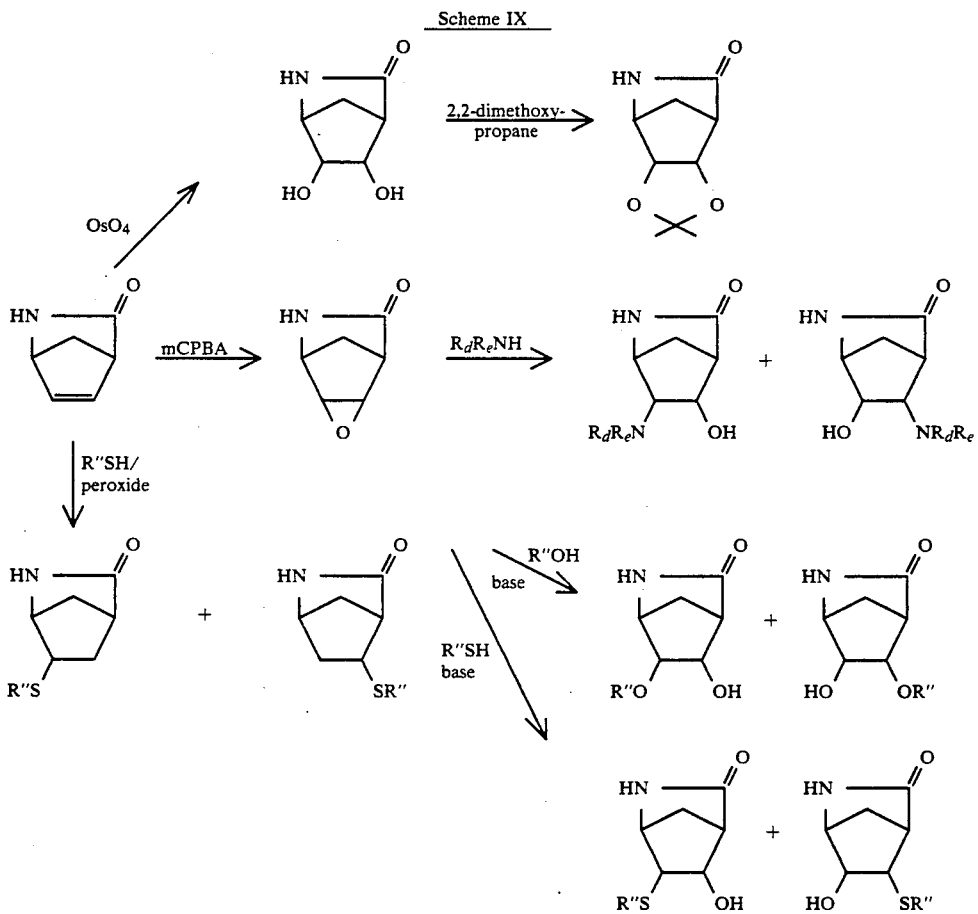

Scheme IX

R" is hydrogen, alkyl, aralkyl or aryl.

2-azabicyclo[2.2.1]hept-5-ene-3-one, *Tetrahedron Lett.*, 22 (25), 2331 (1987), may be cis dihydroxylated by treatment with a catalytic amount of osmium tetroxide in the presence of N-methylmorpholine N-oxide. The resulting glycol is protected as the acetonide by treatment with 2,2-dimethoxypropane.

Treatment of the azabicycloheptenone with m-chloroperbenzoic acid yields the epoxide. The epoxide may be treated with ammonia or an amine to yield a mixture of the two corresponding amino alcohols which may be separated by conventional methods. The epoxide may be treated with an alcohol or a phenol in the presence of base to give a mixture of the alkoxy or aralkoxy alcohols, or the phenoxy alcohols which may be separated to give the individual isomers. The epoxide may also be opened with water to give the trans dihydroxy isomers. The mercapto, alkylthio, arylthio, or aralkylthio alcohols may be prepared by treating the to prevent cross reactivity during the cyclopentenone conversions of Scheme VI or the lactam conversions of Scheme VIII, respectively. These protecting may then be removed by conventional methods either before or after the coupling reaction of Scheme I as necessary.

Hydroxy groups on the cyclopentane ring may be converted to amino groups by methods known in the art. Exemplary preparations are shown in Scheme X, below.

Scheme X

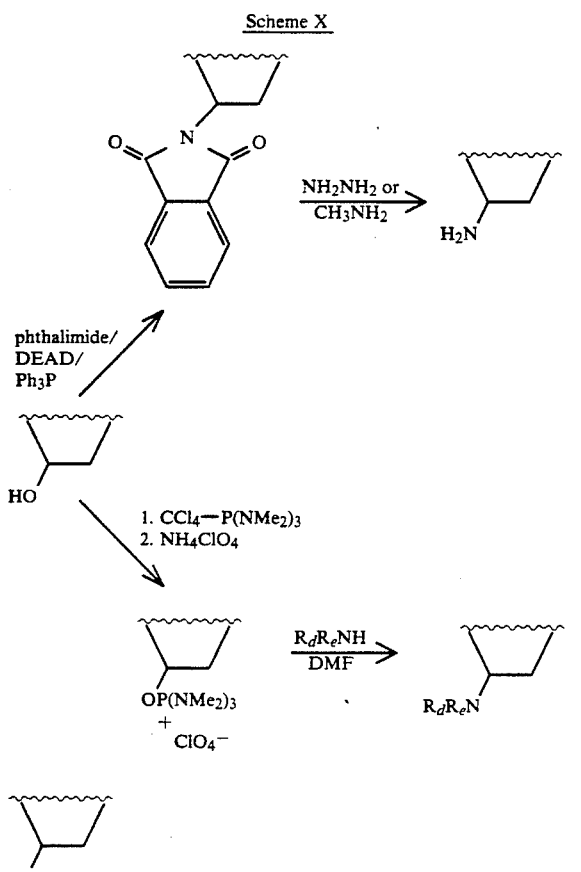

is the appropriately substituted cyclopentane.

The hydroxy compound is treated with phthalimide, triphenylphosphine, and diethyl azodicarboxylate to give the N-substituted phthalimide, Mitsunobu, et al., *J. Am. Chem. Soc.*, 94, 679 (1972), which may then be treated with hydrazine or 40% aqueous methylamine, for example, to give the desired primary amine. Secondary and tertiary amines, as well as primary amines, may be prepared by initially converting the alcohol to the alkyloxyphosphonium perchlorate by treating with hexamethylphosphorous triamide in carbon tetrachloride followed by treatment with ammonium perchlorate, and subsequently treating with the appropriate amine in dimethylformamide, Castro, et al., *Bull. Soc. Chim. Fr.*, 4368 (1971).

Hydroxy groups on the cyclopentane ring may be converted to fluoro, chloro, bromo, and iodo groups by conventional methods (see, for example, March, "Advanced Organic Chemistry," 3rd ed., 382, Wiley, New York (1985). Exemplary preparations are shown in Scheme XI below.

Scheme XI

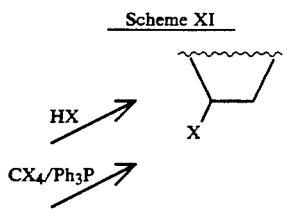

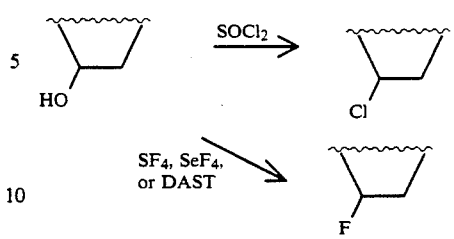

The alcohol may be treated with the halogen acids to yield the desired halide. This reaction is most facile with hydrobromic and hydroiodic acids. The chloro, bromo, or iodo compound may be prepared by treatment of the alcohol, in the presence of triphenylphosphine, with tetrachloromethane, tetrabromomethane, or tetraiodomethane, respectively. The chloro compounds may be prepared by treatment of the hydroxy compound with thionyl chloride. The fluoro group may be introduced by treatment with sulfur tetrafluoride, selenium tetrafluoride or, if milder conditions are necessary or desirable, with diethylaminosulfurtrifluoride, Bozen, et al., *Tetrahedron Lett.*, 1823 (1979).

As noted above, compounds of the present invention have asymmetric carbon atoms which may, individually, be in either the R or S configuration. As a result, the compounds may be obtained as individual enantiomers, racemic mixtures, or, when two or more asymmetric carbon atoms are present, as a mixture of diastereomers. The product may be synthesized as a mixture of isomers and then the desired isomer separated by conventional techniques such as chromatography or fractional crystallization in the case where diastereomers are to be separated, or by chiral chromatography or separation of diastereomeric salts or derivatives of the isomers by fractional crystallization or chromatography in the case of enantiomers, followed by reisolation of the desired product by conventional techniques. Alternatively, synthesis of the compounds may be carried out by known stereospecific processes, or by using the appropriate form of intermediates which would result in obtaining the desired stereoisomer.

A most preferred class of compounds comprises compounds of Formula I wherein A and B are in the $\alpha$ configuration on the cyclopentane ring and Y and Z are in the $\beta$ configuration. The preferred method of preparing such compounds utilizes the cyclopentane starting material having the preferred relative stereochemistry.

The present invention is further explained by the following illustrative examples.

EXAMPLE 1

Preparation of 4$\beta$-(2-pyridyl)amino-2$\alpha$,3$\alpha$-dihydroxycyclopentane-1$\beta$-N-ethylcarboxamide

Step 1

A mixture of 2-fluoropyridine (0.149 g), 4$\beta$-amino-2$\alpha$,3$\alpha$-dimethylmethylenedioxycyclopentane-1$\beta$-N-ethylcarboxamide (0.35 g) (Chen, et al., *Tetrahedron Letters* 30 (41), 5543 (1989)), and potassium fluoride (0.07 g) is heated in a sealed tube at 140° C. for 18 hours, cooled and 70 ml methylene chloride added to the mixture which is washed with brine, dried over magnesium sulfate, filtered, and the solvent removed in vacuo. The residue is flash chromatographed in methylene chloride to give 4β-(2-pyridyl)amino-2α,3α-dimethylmethylenedioxycyclopentane-1β-N-ethylcarboxamide (0.20 g) which is used, without further treatment, in the next step.

Step 2

The product from step 1 above is stirred in 50% formic acid (20 ml) at 50° C. for 3 hours and the solvent evaporated. The residue is taken up in ethyl acetate and saturated sodium bicarbonate solution, the layers separated and the organic layer is dried, filtered, and evaporated. The crude product is purified by flash chromatography to give 4β-(2-pyridyl)amino-2α,3α-dihydroxycyclopentane-1β-N-ethylcarboxamide, m.p. 150°–151° C.

EXAMPLE 2

Preparation of
4β-(3-nitro-2-pyridyl)amino-2α,3α-dihydroxycyclopentane-1β-N-ethylcarboxamide Step 1

A mixture of 2-chloro-3-nitropyridine (0.27 g), triethylamine (2 ml), and 4β-amino-2α,3α-dimethylmethylenedioxycyclopentane-1β-N-ethylcarboxamide (0.40 g) is refluxed in ethanol (40 ml) for 6 hours. The solvent is removed in vacuo and the residue flash chromatographed in 5% methanol/methylene chloride to give 4β-(3-nitro-2-pyridyl)amino-2α,3α-dimethylmethylenedioxycyclopentane-1β-N-ethylcarboxamide as an oil which is used, without further treatment, in the next step.

Step 2

The product from step 1 above is dissolved in 50% formic acid (25 ml), heated at 40° C. for 2 hours and the solvent evaporated. The residue is dissolved in ethyl acetate and the organic phase washed with 5% sodium hydroxide, brine, dried over magnesium sulfate, filtered and the filtrate evaporated. The resulting product is recrystallized from hexane/ethyl acetate to give 4β-(3-nitro-2-pyridyl)amino-2α,3α-dihydroxycyclopentane-1β-N-ethylcarboxamide, m.p. 139°–140° C.

EXAMPLE 3

Preparation of
(−)-4β-(3-nitro-2-pyridyl)amino-2α,3α-dihydroxycyclopentane-1β-N-ethylcarboxamide Step 1

A mixture of 2-chloro-3-nitropyridine (0.35 g), triethylamine (2 ml), and (+)-4β-amino-2α,3α-dimethylmethylenedioxycyclopentane-1β-N-ethylcarboxamide (0.50 g) (Chen, et al., European Pat. Application Publication number 0, 267, 878) is refluxed in ethanol (75 ml) for 6 hours. The solvent is removed in vacuo and the residue flash chromatographed in 5% methanol/methylene chloride to give 4β-(3-nitro-2-pyridyl)amino-2α,3α-dimethylmethylenedioxycyclopentane-1β-N-ethylcarboxamide as an oil which is used, without further treatment, in the next step.

Step 2

The product from step 2 above is dissolved in 50% formic acid (20 ml) and heated at 50° C. for 2 hours. The solvent is evaporated and the residue flash chromatographed in 10% methanol/methylene chloride. The resulting product is recrystallized from hexane/ethyl acetate to give (−)-4β-(3-nitro-2-pyridyl)amino-2α,3α-dihydroxycyclopentane-1β-N-ethylcarboxamide, $[\alpha]_D = -47.35°$; m.p. 157°–158° C.

EXAMPLE 4

Preparation of
(+)-4β-(3-nitro-2-pyridyl)amino-2α,3α-dihydroxycyclopentane-1β-N-ethylcarboxamide When the (−)-4β-amino-2α,3α-dimethylmethylenedioxycyclopentane-1β-N-ethylcarboxamide (Chen, et al., European Pat. Application Publication number 0, 267, 878) is used in place of the (+) isomer in Example 3 above, (+)-4β-(3-nitro-2-pyridyl)amino-2α,3α-dihydroxycyclopentane-1β-N-ethylcarboxamide is prepared, $[\alpha]_D = +48.98°$; m.p. 139°–140° C.

EXAMPLE 5

Preparation of
4β-(3-cyano-2-pyridyl)amino-2α,3α-dihydroxycyclopentane-1β-N-ethylcarboxamide Step 1

A mixture of 2-chloro-3-cyanopyridine (0.49 g), 4β-amino-2α,3α-dimethylmethylenedioxycyclopentane-1β-N-ethylcarboxamide (0.62 g), and triethylamine (3.5 ml) is refluxed in ethanol (40 ml) for 41 hours and treated as in step 1 of Example 2 above to give 4β-(3-cyano-2-pyridyl)amino-2α,3α-dimethylmethylenedioxycyclopentane-1β-N-ethylcarboxamide.

Step 2

The product from step 1 above is treated as in step 2 of Example 2 above to give 4β-(3-cyano-2-pyridyl)amino-2α,3α-dihydroxycyclopentane-1β-N-ethylcarboxamide, m.p. 152°–153° C.

EXAMPLE 6

Preparation of
4β-(4-amino-3-nitro-2-pyridyl)amino-2α,3α-dihydroxycyclopentane-1β-N-ethylcarboxamide Step 1

A mixture of 4-amino-2-chloro-3-nitropyridine (0.11 g), 4β-amino-2α,3α-dimethylmethylenedioxycyclopentane-1β-N-ethylcarboxamide (0.098 g), and triethylamine (0.1 ml) is refluxed in nitromethane (5 ml) for 5 hours. The solvent is removed and the residue flash chromatographed in 2% methanol/chloroform to give 4β-(4-amino-3-nitro-2-pyridyl)amino-2α,3α-dimethylmethylenedioxycyclopentane-1β-N-ethylcarboxamide which is used, without further treatment, in the next step.

Step 2

The product from step 1 above is treated with formic acid as in step 2 of Example 2 to give 4β-(4-amino-3-nitro-2-pyridyl)amino-2α,3α-dihydroxycyclopentane-1β-N-ethylcarboxamide, m.p. 159°–160° C.

EXAMPLE 7

Preparation of
4β-(2-nitrophenyl)amino-2α,3α-dihydroxycyclopentane-1β-N-ethylcarboxamide Step 1

A mixture of 2-fluoronitrobenzene (0.680 g), 4β-amino-2α,3α-dimethylmethylenedioxycyclopentane-1β-N-ethylcarboxamide (1.1 g), and potassium fluoride (0.28 g) is heated at 140° C. for 90 minutes. The mixture is cooled, dissolved in methylene chloride, and washed with brine. The organic phase is dried over magnesium sulfate, filtered, and the solvent evaporated in vacuo. The residue is flash chromatographed in 5% methanol/-methylene chloride to give 4β-(2-nitrophenyl)amino-2α,3α-dimethylmethylenedioxycyclopentane-1β-N-ethylcarboxamide which is used, without further treatment, in the next step.

Step 2

The product from step 1 above is stirred in 50% formic acid at 50° C. for 2 hours. The solvent is removed and the residue flash chromatographed in 15% methanol/methylene chloride to give 4β-(2-nitrophenyl)amino-2α,3α-dihydroxycyclopentane-1β-N-ethylcarboxamide, m.p. 185°–186° C.

EXAMPLE 8

Preparation of 4β-(4-nitro-2-pyridyl)amino-2α,3α-dihydroxycyclopentane-1β-N-ethylcarboxamide When 2-chloro-4-nitropyridine is substituted for the 3-nitro isomer in Example 2, 4β-(4-nitro-2-pyridyl)amino-2α,3α-dihydroxycyclopentane-1β-N-ethylcarboxamide is prepared, m.p. 187°–188° C.

EXAMPLE 9

Preparation of 4β-(3-Methyl-4-nitro-2-pyridyl)amino-2α,3α-dihydroxycyclopentane-1β-N-ethylcarboxamide When 2-chloro-3-methyl-4-nitropyridine is substituted for the 3-nitro isomer in Example 2, 4β-(3-methyl-4-nitro-2-pyridyl)amino-2α,3α-dihydroxycyclopentane-1β-N-ethylcarboxamide is prepared, m.p. 166°–167° C.

EXAMPLE 10

When the aryl halides listed in Table A, below, are substituted for 2-chloro-3-nitropyridine in Example 2, above, then the corresponding products listed in Table B, below, are prepared, respectively.

TABLE A 2-chloro-3-nitro thiophene
2-chloro-5-nitro-thiophene
2-chloro-3-nitroquinoline
2-chloropyrimidine
2-chloropyrazine

TABLE B

4β-(3-nitro-2-thienyl)amino-2α,3α-dihydroxycyclopentane-1β-N-ethylcarboxamide
4β-(5-nitro-2-thienyl)amino-2α,3α-dihydroxycyclopentane-1β-N-ethylcarboxamide
4β-(3-nitro-2-quinolinyl)amino-2α,3α-dihydroxycyclopentane-1β-N-ethylcarboxamide
4β-(2-pyrimidyl)amino-2α,3α-dihydroxycyclopentane-1β-N-ethylcarboxamide
4β-(2-pyrazinyl)amino-2α,3α-dihydroxycyclopentane-1β-N-ethylcarboxamide Compounds of the present invention exhibit blood pressure lowering activity and are useful as antihypertensive agents for the treatment of high blood pressure. Exemplary test procedures which are useful in determining the antihypertensive effect of compounds of the present invention are described below.

IN VIVO MEAN ARTERIAL BLOOD PRESSURE (MAP) AND HEART RATE (HR) DETERMINATIONS IN NORMOTENSIVE ANESTHETIZED AND SPONTANEOUSLY HYPERTENSIVE RAT

1. Anesthetized Rat

Normotensive rats were anesthetized with sodium pentobarbital (50 mg/kg, i.p.) and placed on a heated surgical table. Cannulas were inserted into the femoral artery and veined to allow the measurement of arterial pressure and to facilitate the intravenous administration of test compounds. The animals was allowed to equilibrate for 10 minutes after surgery. Mean arterial pressure was continuously measured and recorded and heart rate was monitored using the arterial pressure pulse to trigger a cardiotachometer. After baseline parameters were established and recorded, increasing doses (1, 3, 10, 30, 100, 300 and 1000 μg/kg) of the compound of this invention to be tested were administered intravenously. Maximal changes in the cardiovascular parameters were observed after each dose of the compound. Only one compound was administered per rat. The potency of the compounds to lower heart rate and mean arterial pressure were assessed by determining the dose of the agent necessary to lower the heart rate or arterial pressure by 25% ($ED_{25}$).

2. Spontaneously Hypertensive Rat (SHR)

The oral antihypertensive activity of compounds of this invention were examined in conscious spontaneously hypertensive rats. The rats were anesthetized with sodium pentobarbital (50 mg/kg i.p.). A telemetry transducer was implanted into the rats abdomen via midline incision. The cannula of the transducer was inserted into the abdominal aorta to allow direct measurement of arterial pressure in the conscious SHR. The transducer was secured to the abdominal wall. After recovery from surgery (minimum of seven days), the SHR were placed on a receiver plate and the transducer/transmitter was activated. Systolic, diastolic and mean arterial pressure and heart rate were recorded for 1.5 hours in the unrestrained conscious rat to establish a stable baseline. Each rat then received a single dose of the compound of this invention to be tested, or vehicle, and changes in arterial pressure and heart rate were monitored for 20 hours and recorded.

The intravenous antihypertensive activities of compounds of the present invention, as measured by the anesthetized rat procedure, are described in Table I below.

TABLE I

| Compound | $ED_{25}$ (MAP) μg/Kg | $ED_{25}$ (HR) μg/KG |
|---|---|---|
| 4β-(3-Nitro-2-pyridyl)amino-2α, 3α-dihydroxycyclopentane-1β-N-ethylcarboxamide | 17 | >60[1] |
| 4β-(3-Cyano-2-pyridyl)amino-2α, 3α-dihydroxycyclopentane-1β-N-ethylcarboxamide | 18 | >30 |
| 4β-(4-Amino-3-nitro-2-pyridyl)amino-2α, 3α-dihydroxycyclopentane-1β-N-ethylcarboxamide | 6.1 | >1000 |
| 4β-(4-Nitro-2-pyridyl)amino-2α, 3α-dihydroxycyclopentane-1β-N-ethylcarboxamide | 51 | >30 |
| 4β-(3-Methyl-4-nitro-2-pyridyl)amino-2α, 3α-dihydroxycyclopentane-1β-N- | 124 | >1000 |

TABLE I-continued

| Compound | ED$_{25}$ (MAP) µg/Kg | ED$_{25}$ (HR) µg/KG |
|---|---|---|
| ethylcarboxamide | | |

[1]> (greater than) indicates that, at the doses tested, the heart rate was not lowered to the extent of 25%.

The oral antihypertensive activity of compounds of the present invention, as measured in the spontaneously hypertensive rat, is described in Table II below, which presents the mean arterial pressure and change from base line heart rate after 1 hour for vehicle, and two compounds of the present invention.

TABLE II

| Hours post dose | Change in Mean Arterial Blood Pressure (mm Hg) | Change in Heart Rate (beats/min) |
|---|---|---|
| 1 | [a] 2.0 | −21.6 |
| | [b] −61.3 | 54.3 |
| | [c] −24.0 | 8.00 |

[a] Vehicle
[b] 4β-(3-nitro-2-pyridyl)amino-2α, 3α-dihydroxycyclopentane-1β-N-ethylcarboxamide
[c] 4β-(4-amino-3-nitro-2-pyridyl)amino-2α, 3α-dihydroxycyclopentane-1β-N-ethylcarboxamide The compounds of this invention can be normally administered orally or parenterally, in the treatment of patients suffering from hypertension. As used herein, the term "patients" includes humans and other mammals.

The compounds of this invention, preferably in the form of a salt, may be formulated for administration in any convenient way, and this invention includes within its scope pharmaceutical compositions containing at least one compound according to this invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of the compound of this invention to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for administration by intramuscular and subcutaneous injection. The aqueous solutions, including those of the salts dissolved in pure distilled water, are suitable for administration by intravenous injection, provided that their pH is properly adjusted, and that they are suitably buffered, made isotonic with sufficient saline or glucose and sterilized by heating or by microfiltration.

The dosage regimen used in carrying out the methods of this invention is that which insures maximum therapeutic response until improvement is obtained and thereafter the minimum effective level which gives relief. Thus, in general, the dosages are those that are therapeutically effective in lowering blood pressure in the treatment of hypertension. In general, the oral dose may be between about 0.1 and about 100 (preferably in the range of 1 to 10 mg/kg), and the i.v. dose about 0.01 to about 10 mg/kg (preferably in the range of 0.1 to 5 mg/kg), bearing in mind, of course, that in selecting the appropriate dosage in any specific case, consideration must be given to the patient's weight, general health, age and other factors which may influence response to the drug.

The compounds of this invention may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute hypertension. Such treatment may be followed by intravenous infusion of the active compound and the amount of compound infused into such a patient should be effective to achieve and maintain the desired therapeutic response.

What is Claimed is:
1. A compound of the formula

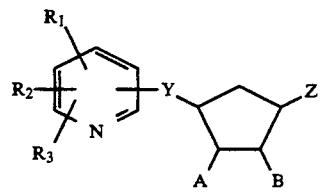

wherein
$R_1$, $R_2$, and $R_3$ are independently nitro, cyano, carboxy, carboalkoxy, carboaryloxy, carboaralkoxy, carbamoly, alkylcarbamoyl, dialkylcarbamoyl, thiocarbamoyl, alkylthiocarbamoyl, dialkylthiocarbamoyl, halo, alkoxy, alkylthio, acyl, aryl, alkyl, amino, alkylamino, dialkylamino or hydrogen;

Y is oxygen, sulfur, or —$NR_y$— where $R_y$ is hydrogen or alkyl;

A and B are independently hydrogen, hydroxy, alkoxy, aralkoxy, aryloxy, mercapto, alkylthio, arylthio, aralkythio, amino, alkylamino, dialkylamino or halo, provided that A and B are not both hydrogen; and Z is carbamoyl, alkylcarbamoyl, dialkylcabamoyl, thiocarbamoyl, alkylthiocarbamoyl, dialkylthiocarbamoyl, mercaptomethyl, alkylthiomethyl, alkoxymethyl, aryloxymethyl, arylthiomethyl, alkoxy, aryloxy, aralkoxy, amino, alkylamino, dialkylamino, mercapto, alkylthio, cyano, carboxy, carboalkoxy, carboaralkoxy, carboaryloxy, alkyl, aryl, aminomethyl, alkylaminomethyl or dialkylaminomethyl;

and wherein alkyl has 1-20 carbon atoms and aryl is phenyl or naphthyl; or a pharmaceutically acceptable salt thereof.

2. A compound of claim 1 wherein
$R_1$ is nitro or cyano.

3. A compound of claim 2 wherein
Z is carbamoyl, alkylcarbamoyl, dialkylcarbamoyl, thiocarbamoyl, alkylthiocarbamoyl, dialkylthiocarbamoyl, cyano, carboxy, carboalkoxy, carboaralkoxy or carboaryloxy.

4. A compound of claim 3 wherein
$R_2$, and $R_3$ are independently hydrogen, nitro, cyano, carboxy, carboalkoxy, carboaryloxy, carboaralkoxy, carbamoyl, alkylcarbamoyl, dialkylcarbamoyl, thiocarbamoyl, alkylthiocarbamoyl or dialkylthiocarbamoyl;
Y is —$NR_y$— where $R_y$ is hydrogen or alkyl;

A and B are independently hydrogen, hydroxy, mercapto, amino or fluoro provided that A and B are not both hydrogen; and Z is carbamoyl, alkylcarbamoyl, dialkylcarbamoyl, thiocarbamoyl, alkylthiocarbamoyl or dialkylthiocarbamoyl.

5. A compound according to claim 2 which is (+,−)-N-ethyl-4β-[(4-amino-3-nitro-2-pyridyl)amino]-2α,3α-dihydroxy-1β-cyclopentanecarboxamide.

6. A compound according to claim 2 which is (+,−)-N-ethyl-4β-[3-nitro-2-pyridyl)amino]-2α,3,α-dihydroxy-1β-cyclopentanecarboxamide.

7. A compound according to claim 2 which is (−)-N-ethyl-4β-[(3-nitro-2-pyridyl)amino]-2α,3α-dihydroxy-1β-cyclopentanecarboxamide.

8. A compound according to claim 2 which is (+)-N-ethyl-4β-[(3-nitro-2-pyridyl)amino]- 2α,3α-dihydroxy-1β-cyclopentanecarboxamide.

9. A compound according to claim 2 which is (+,−)-N-ethyl-4β-[(2-pyridyl)amino]-2α,3α-dihydroxy-1β-cyclopentanecarboxamide.

10. A compound according to claim 2 which is (+,−)-N-ethyl-4β-[(3-cyano-2-pyridyl)amino]-2α,3α-dihydroxy-1α-cyclopentanecarboxamide.

11. A compound according to claim 2 which is (+,−)-N-ethyl-4β-[(4-nitro-2-pyridyl)amino]-2α,3α-dihydroxy-1β-cyclopentanecarboxamide.

12. A pharmaceutical composition comprising an antihypertensive effective amount of a compound according to claim 1 or a pharmaceutically acceptable salt thereof; and a pharmaceutically acceptable carrier thereof.

* * * * *